United States Patent [19]

Paudler

[11] Patent Number: 5,242,417
[45] Date of Patent: Sep. 7, 1993

[54] SELF CLOSING HINGED SYRINGE GUARD

[76] Inventor: Gary M. Paudler, P.O. Box 70, Summerland, Calif. 93067

[21] Appl. No.: 819,834

[22] Filed: Jan. 13, 1992

[51] Int. Cl.[5] ............................................. A61M 5/32
[52] U.S. Cl. ................................. 604/192; 604/263; 206/365
[58] Field of Search ............... 604/187, 192, 263, 110; 128/919; 206/364–366

[56] References Cited

U.S. PATENT DOCUMENTS

| | | | |
|---|---|---|---|
| 4,664,259 | 5/1987 | Landis | 206/365 |
| 4,820,277 | 4/1989 | Norelli | 604/192 |
| 4,838,871 | 6/1989 | Luther | 604/192 |
| 4,976,699 | 12/1990 | Gold | 604/192 |
| 4,982,842 | 1/1991 | Hollister | 206/365 |
| 5,151,089 | 9/1992 | Kirk et al. | 604/192 |
| 5,152,751 | 10/1992 | Kozlowski | 604/192 |
| 5,188,611 | 2/1993 | Orgain | 604/192 |
| 5,197,954 | 3/1993 | Cameron | 604/110 |

FOREIGN PATENT DOCUMENTS

| | | | |
|---|---|---|---|
| 3713754 | 11/1988 | Fed. Rep. of Germany | 604/192 |
| 9001348 | 2/1990 | World Int. Prop. O. | 604/192 |

Primary Examiner—C. Fred Rosenbaum
Assistant Examiner—Mark O. Polutta
Attorney, Agent, or Firm—Marvin E. Jacobs

[57] ABSTRACT

A syringe is molded with an integral needle cover or guard that pivots about a main living hinge on the side of the syringe near the base of the needle. A tension spring formed from an L shaped integrally molded part of the syringe and guard extends from a location closer to the syringe than the main living hinge to the center part of the pivoting guard. The user, while holding the syringe with one hand, can extend a finger to initiate rotation of the guard toward the needle. This extends the tension spring at first, but beyond a certain angle, the tension spring contracts again, pulling the guard the rest of the way into a position surrounding the needle.

15 Claims, 2 Drawing Sheets

SELF CLOSING HINGED SYRINGE GUARD

TECHNICAL FIELD

This invention pertains to protective covers for so-called disposable medical sharps such as scalpels, catheters, and syringes. More particularly, a self closing cover is disclosed that obviates the need for users to move or place their fingers in close proximity to the sharp blade or needle.

BACKGROUND OF THE INVENTION

New sharps are supplied with a protective cap or sheath to protect the user from accidental injury. This cap is removed prior to use and replaced afterwards to avoid danger. The used instrument may be contaminated with infectious material after use and this provides an even more compelling reason to recap the disposable sharp. However, it is the act of recapping that most often causes accidental pricks, injury, and possible infections.

For ease of description, this art and this invention are described in the context of use with syringes which are the most common and widely used disposable sharps. The prior art recognizes numerous kinds of protective caps, covers, and sheaths for syringes. For example, Hollister U.S. Pat. No. 4,982,842 discloses a syringe with a slotted cover for the needle that hinges on the side of the syringe by means of a thin plastic living hinge. After use, the cover is in a convenient position to be rotated to a needle-enclosing configuration. However, the user must grasp the cover with his fingers and move it toward the needle. This is dangerous because any movement of the fingers in close proximity to the needle point inevitably invites a mistake and an injury. Millions of needles are used and accidents will happen eventually. The Hollister patent itself references many other prior art patents relevant to this field.

Another class of prior art sheaths uses two piece clamshell arrangements that close about the needle from both sides, typified by Norelli U.S. Pat. Nos. 4,820,277 and 4,909,792, Cole U.S. Pat. No. 4,944,731, and Landis U.S. Pat. No. 4,664,259. These too are manually operable, requiring the user to squeeze the cover halves toward the needle to effect some latching or locking action. Again, the fingers must be used to apply force close to, and in the direction of, the sharp part of the needle. If the plastic parts fail or distort, or if the users fingers slip, accidental contact with the needle is far too easy.

A pivoting needle sheath is disclosed by Luther U.S. Pat. No. 4,838,871, which is moved with the fingers toward the needle, again requiring placing the fingers in close proximity to the needle and moving them. See also Unger U.S. Pat. No. 4,872,552.

The present invention avoids having to ever place or move the user's finger near the sharp needle or scalpel blade by employing a self closing sheath that, once started, moves itself into position about the needle or blade.

SUMMARY OF THE INVENTION

Briefly, the present invention contemplates a syringe guard that pivots on the side of the syringe and into position surrounding the sharp end of the needle. The guard pivots about a main guard pivot hinge with an axis that is orthogonal to the length of the syringe and displaced away from the syringe so as to provide clearance for a tension spring member. The tension spring member also pivots on the side of the syringe, about a first tension spring hinge that is located farther away from the needle than the guard, but at a position closer to the syringe than the main guard pivot hinge. The other end of the tension spring connects to the guard by means of a second tension spring hinge at a location just beyond the main guard pivot hinge.

With this geometry, the guard can be pivoted part way toward the needle which causes the tension spring to elongate and rotate about the two tension spring hinges. At this point, the first and second tension hinges come into alignment with the main guard hinge. Beyond this point, the tension spring contracts again, pulling the guard into engagement with the needle, by itself, without additional pushing by the user. Since the user need only push the guard part way, to get it started, the user never places a finger close to the sharp end of the needle. And the user never needs to apply force to the guard near the sharp end of the needle in order to effect closing or latching. Hence, the risk of accidental slips or movements toward the needle point is reduced to near zero.

This geometry also allows single handed operation because the hand that holds the syringe can close the guard around the needle simply by extending a thumb or finger upwards against the hinge end of the guard. The remaining fingers firmly grasp the syringe and keep it steady. Such an action is not possible, or is very dangerous, if the guard must be manipulated at its remote end near the needle point.

In addition to being self closing, the syringe guard of this invention is designed to be molded from a single piece of plastic, indeed even as an integral part of the syringe body itself in order to be very low cost. Thus, a great increase in safety is achieved at little additional expense. Other advantages and benefits are described in the following detailed description and the drawings referenced thereby.

DETAILED DESCRIPTION OF THE INVENTION

Figure 1:
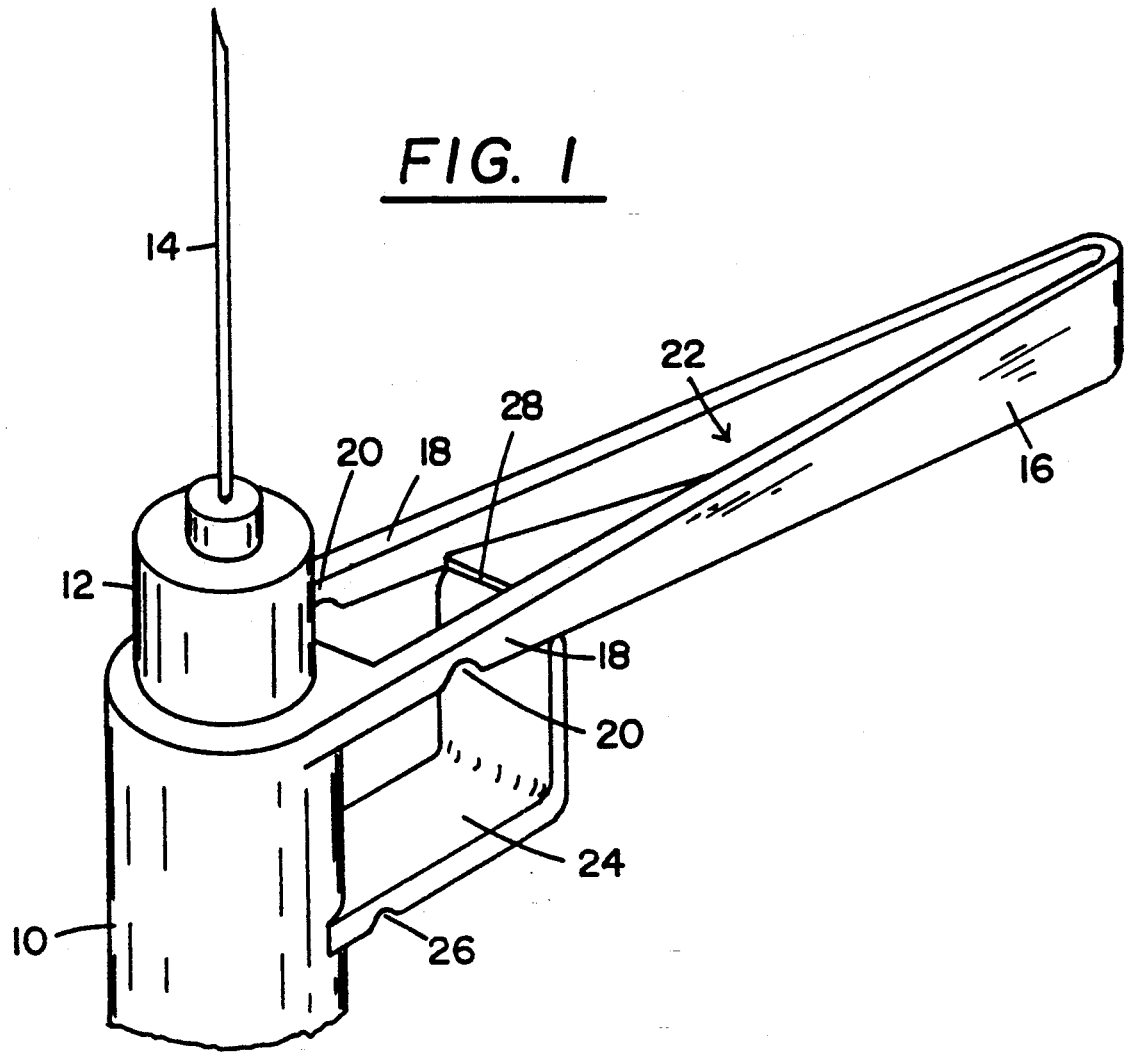
FIG. 1 is a perspective view of the needle carrying end of a syringe with the hinged self closing needle guard of the present invention molded as an integral part thereof.

FIG. 1 shows the top portion of a typical syringe 10 with a conventional hub 12 inserted therein by threads or other means well known to those in the art. A needle 14 is supported by hub 12, also in a conventional manner. A self closing guard 6 is molded as an integral part of the syringe 10 in the preferred embodiment, but it could be formed as part of hub 12 as well. Alternatively, guard 16 could be molded as part of an intermediate cylinder that connects at one end to the syringe 10 and accepts at the other end hub 12 and needle 14. However, the most efficient arrangement is depicted in FIG. 1.

Syringe 10 is usually molded from a plastic such as polypropylene or the like. This plastic is also suitable for the guard structure. Hence, the present invention is designed so that the syringe and the guard structure are molded at the same time as an integral one piece unit. Thus, very little extra cost is introduced, the additional plastic being minimal.

Guard 16 is connected to opposite sides of syringe 10 by means of a pair of arms 18. Arms 18 have reduced thickness regions that define a living hinge 20. The axis of flexure of hinge 20 is orthogonal to the elongate axis of the syringe body 10 so that guard 16 is allowed to bend only toward the syringe axis and into a needle 14 surrounding position. Since arms 18 attach to the outermost perimeter of the syringe body, the widest possible hinge line 20 is created to insure the most accurate alignment of the guard 16 with needle 14. Guard 16 includes a needle enclosing slot 22 shaped to fit over and around needle 14 and especially over the sharp point of the needle so that no possibility of contact with the point remains.

Hinge 20 is displaced away from the side of the syringe 10 so as to afford clearance for a tension spring member 24. Tension spring 24 is hinged to the side of the syringe with a first living hinge 26 molded from a reduced thickness region of the spring 24. Spring 24 is hinged to the guard 16 with a second living hinge 28, again formed from a reduced thickness region of the spring. Spring 24 is molded into a shape other than straight from hinge 26 to hinge 28. It could be wavy, or stepped, or continuously curved. The shape is shown as an L shape in FIG. 1, which is easy to mold and effective as a tension spring member. Hinge 26 is closer to the syringe than hinge 20 to establish the proper geometry to make the guard self closing.

Figure 2:
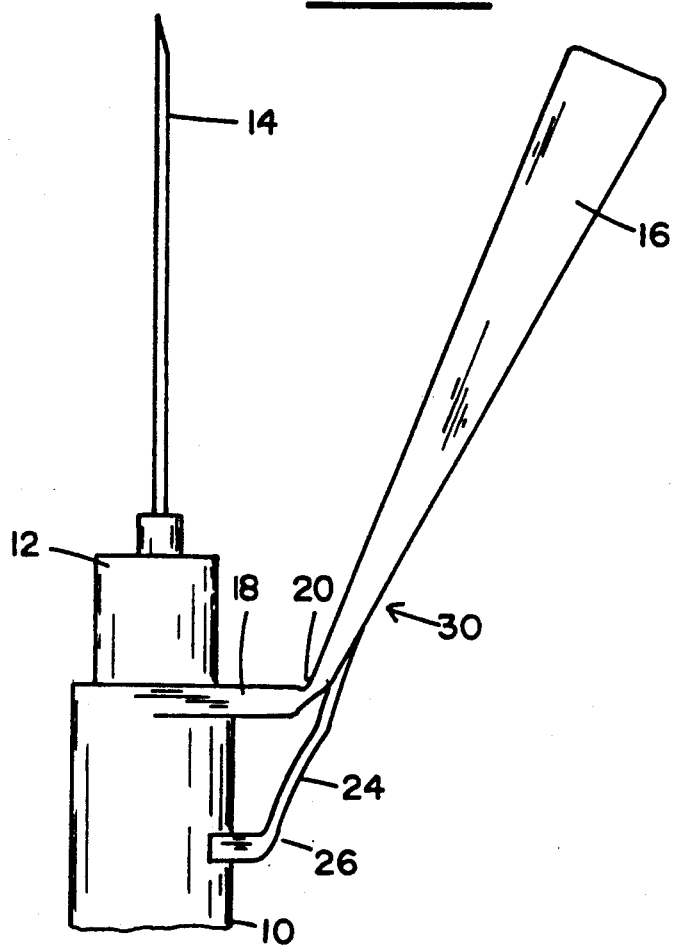
FIG. 2 is an elevational side view of the structure of FIG. 1, but with the guard rotated part wy toward the needle to the point where the guard will continue to rotate by itself toward and around the sharp portion of the needle.
Figure 3:
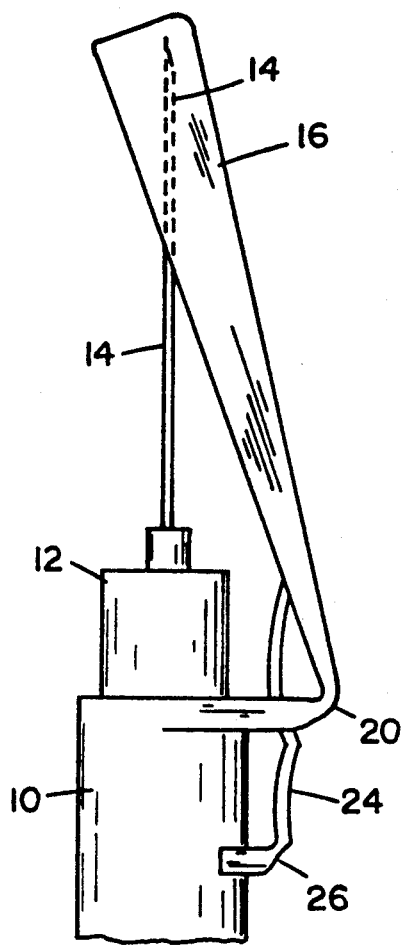
FIG. 3 is a side view similar to FIG. 2 but with the guard fully rotated against the needle.

FIG. 2 shows how the closing process is initiated. The user, while grasping the syringe 10 firmly in the hand, simply extends a thumb or finger upward against the underside of guard 16 generally in the area indicated by numeral 30 in FIG. 2. The guard is rotated about main hinge 20 to approximately the angle shown in FIG. 2. The tension spring 24 is stretched in the process, being distorted from the relaxed L shape of FIG. 1 to the nearly straight shape in FIG. 2. At this point, hinges 26, 20, and 28 are linearly aligned and tension spring 24 is at the maximum extension. Beyond the point shown in FIG. 2, spring 24 pulls guard 16 the rest of the way to a position over and around needle 14 as shown in FIG. 3.

Since the guard is self closing, it is important to insure that the guard always rotates directly toward the needle so that needle 14 always enters slot 22. As described above, hinge 20 is designed to have the maximum width so as to provide the widest possible base for the guard. Moreover, tension spring 24 is formed from a generally flat member that is fairly rigid in a direction orthogonal to the syringe. Thus, spring 24 further locates guard 16 in a needle aligned position. Any sideways deflection of the guard is resisted by flat spring 24. Furthermore, the flatness of spring 24 causes hinges 26 and 28 to have well established axes of rotation which are parallel to the axis of main hinge 20. Finally, after spring 24 begins to pull guard 16 toward needle 14, the central location of the spring 24, between arms 18, guarantees a balanced closing force which is directed toward the center of the syringe. All of these geometric features cooperate to produce a self closing guard that can only rotate in one direction, straight to the needle 14.

Area 30 is remote from the sharp end of needle 14 so that the user never applies pressure in a direction or location proximate the sharp end. In addition, the structure of the guard is physically interposed between the users finger and the needle so that any slip of the finger is deflected away from the needle. Guard 16 is aligned with the needle automatically, without the need for visual reference by the user, by the orthogonal hinge 20 and the sloping interior walls of slot 22. Thus, the attention of the user is not diverted from his main task of treating the patient. As can be seen in FIG. 3, the guard pivots over the end of the needle so that the needle can not be removed from the syringe. The used syringe and needle are then disposed of as a unit.

Figure 5:
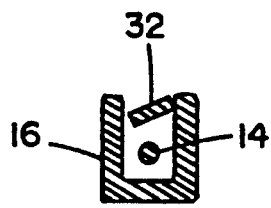
FIG. 5 is a cross sectional view through the guard to illustrate a needle trapping flap that may be molded inside the guard to prevent the guard from being accidentally bent away from the needle after engagement.

The guard may be V or U shaped inside. As shown in FIG. 5, a small flap 32 may be molded to the inside of the guard near the end where the needle enters. The angle of flap 32 is such that as the guard snaps into place about needle 14, flap 32 is pushed aside by the needle. Afterwards, the flap 32 returns to the position shown in FIG. 5, trapping needle 14 inside for safe disposal.

Figure 4:
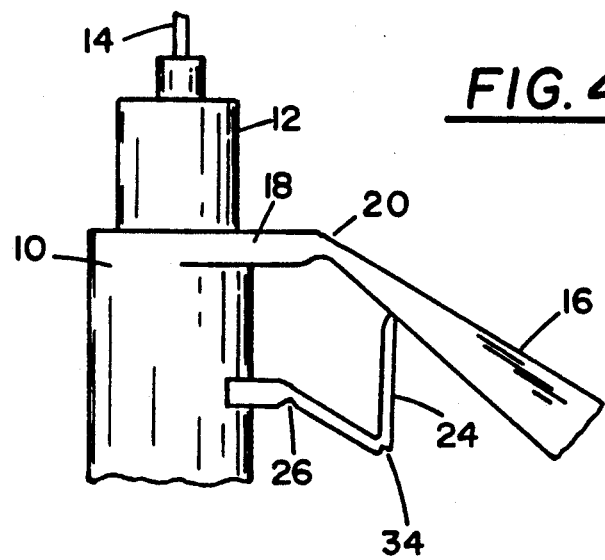
FIG. 4 is another side view, but showing an alternative embodiment wherein an additional hinge in the tension spring member allows the guard to be rotated in the opposite direction away from the needle, if desired.

An alternative embodiment of the invention is shown in FIG. 4. An additional reduced thickness region is molded into tension spring member 24 to create another living hinge 34. Hinge 34 makes it easier for tension spring 24 to fold downward so that the guard 16 may be pivoted away from the needle, as shown in FIG. 4, if additional clearance is required to properly operate the syringe. Numerous other variations may occur to those skilled in the art that remain within the scope and spirit of the invention. Accordingly, the invention should not be limited to the specific arrangements described above except in accordance with the following claims and their equivalents.

I claim:

1. A syringe with a self closing guard comprising:
   a syringe having an elongate axis and adapted to support a needle at one end;
   a guard with a slot therein shaped to accept said needle within, said guard pivoted on said syringe at a location near said one end and about a main hinge, the axis of said main hinge being orthogonal to said elongate axis and displaced away from said elongate axis by a short distance; and
   a tension spring member extending from a first spring hinge to a second spring hinge, said first spring hinge mounted to the syringe on the same side of the syringe as said main hinge and at a distance closer to said elongate axis than said main hinge and at a location along the syringe on the opposite side of the main hinge from said needle, said second spring hinge mounted to the guard at a place proximate to said main hinge so as to pull said guard into position with the needle inside said slot when the guard is rotated about said main hinge part of the way toward said needle.

2. The guard of claim 1 in which said syringe, said guard, said tension spring member, said main hinge, said first spring hinge, and said second spring hinge are integrally molded from a plastic material.

3. The guard of claim 2 in which said plastic is polypropylene or the like.

4. The guard of claim 1 in which said main hinge comprises first and second arms extending from said guard respectively to opposite sides of said syringe, each of said arms having a reduced thickness region therein to create a living hinge.

5. The guard of claim 4 in which said first and second spring hinges comprises reduced thickness regions of said tension spring member.

6. The guard of claim 5 in which said first and second spring hinges comprise reduced thickness regions of said tension spring member.

7. The guard of claim 6 in which said tension spring member comprises a generally flat member so as to resist sideways deflections of said guard.

8. The guard of claim 7 in which said second spring hinge connects to the guard at a location between said first and second arms to insure a balanced closing pulling force on said guard.

9. The guard of claim 8 in which said syringe, said guard, said tension spring member, said main hinge, said first spring hinge, and said second spring hinge are integrally molded from a plastic material.

10. The guard of claim 9 in which said plastic is polypropylene or the like.

11. The guard of claim 10 including a needle trapping bendable flap molded inside said slot in said guard.

12. The guard of claim 1 including a reduced thickness region in said tension spring member that forms a third spring hinge so that said guard may be more easily rotated away from the needle if necessary.

13. The guard of claim 8 including a reduced thickness region in said tension spring member that forms a third spring hinge so that said guard may be more easily rotated away from the needle if necessary.

14. The guard of claim 10 including a reduced thickness region in said tension spring member that forms a third spring hinge so that said guard may be more easily rotated away from the needle if necessary.

15. The guard of claim 14 including a needle trapping bendable flap molded inside said slot in said guard.

* * * * *